(12) United States Patent
Hacker et al.

(10) Patent No.: US 12,711,616 B2
(45) Date of Patent: Aug. 18, 2026

(54) DEVICE FOR POSITIONING AN IMPLANT IN A TARGET AREA OF AN EYE

(71) Applicants: Carl Zeiss Meditec, Inc., Dublin, CA (US); Carl Zeiss Meditec AG, Jena (DE)

(72) Inventors: Martin Hacker, Jena (DE); Christoph Hauger, Aalen (DE); Scott Meyer, Livermore, CA (US)

(73) Assignee: Carl Zeiss Meditec AG, Jena (DE)

( * ) Notice: Subject to any disclaimer, the term of this patent is extended or adjusted under 35 U.S.C. 154(b) by 511 days.

(21) Appl. No.: 18/246,129

(22) PCT Filed: Sep. 21, 2021

(86) PCT No.: PCT/EP2021/075900
§ 371 (c)(1),
(2) Date: Mar. 21, 2023

(87) PCT Pub. No.: WO2022/058606
PCT Pub. Date: Mar. 24, 2022

(65) Prior Publication Data

US 2023/0368380 A1 Nov. 16, 2023

Related U.S. Application Data

(60) Provisional application No. 63/080,801, filed on Sep. 21, 2020.

(51) Int. Cl.
*G06T 7/00* (2017.01)
*A61F 9/00* (2006.01)

(52) U.S. Cl.
CPC .......... *G06T 7/0012* (2013.01); *A61F 9/0017* (2013.01); *G06T 2207/30041* (2013.01)

(58) Field of Classification Search
CPC ......... A61B 3/102; A61B 34/20; A61B 90/20; A61F 9/00781; A61F 9/007;
(Continued)

(56) References Cited

U.S. PATENT DOCUMENTS 3,788,327 A 1/1974 Donowitz
6,881,198 B2 4/2005 Brown
(Continued)

FOREIGN PATENT DOCUMENTS

DE 102018213872 11/2019
EP 3403622 11/2018
(Continued)

OTHER PUBLICATIONS

International Search Report (English translation) and Written Opinion for PCT/EP2021/075900 date mailed Dec. 23, 2021.
(Continued)

*Primary Examiner* — Justin W Rider
(74) *Attorney, Agent, or Firm* — DeWitt LLP

(57) ABSTRACT

The present invention relates to a device for positioning an implant in an eye. The device includes an image recording unit, an image display unit, a control and evaluation unit and an implantation tool. The image recording unit provides images of the target area in the eye. The control and evaluation unit to detects eye structures in the images of the target area, to propose or to select a target region for the implant and to generate navigation data for the introduction of the implantation tool into the target region. The proposed device can be used for positioning implants in any regions of the eye.

18 Claims, 1 Drawing Sheet

(58) Field of Classification Search
CPC ......... A61F 2/1662; A61F 2009/00851; G01B 9/02091; G06T 2207/10101
USPC ........................................................... 348/78
See application file for complete search history.

(56) References Cited

U.S. PATENT DOCUMENTS

| | | | |
|---|---|---|---|
| 8,926,510 B2 | 1/2015 | Marshall et al. | |
| 2015/0077528 A1 | 3/2015 | Awdeh | |
| 2017/0276926 A1 | 9/2017 | Ootsuki et al. | |
| 2018/0098812 A1 | 4/2018 | Ootsuki | |
| 2019/0117459 A1 | 4/2019 | Berlin | |
| 2020/0146885 A1 | 5/2020 | Ootsuki et al. | |
| 2024/0065787 A1 * | 2/2024 | Lech | A61B 17/07207 |

FOREIGN PATENT DOCUMENTS

| | | |
|---|---|---|
| WO | WO2004110391 | 12/2004 |
| WO | WO2016109639 | 7/2016 |
| WO | WO2017108498 | 6/2017 |

OTHER PUBLICATIONS

Denis, Phillipe, MD et al., “A First-in-Human Study of the Efficacy and Safety of MINIject in Patients with Medically Uncontrolled Open-Angle Glaucoma (START-I)., American Academy of Ophthalmology”, vol. 2, Issue 5, (2019).

Li, Peng, et al.., Phase-Sensitive Optical Coherence Tomography characterization of Pulse-Induced Trabecular Meshwork Displacement in ex vivo Nonhuman Primate Eyes, Journal of Biomedical Optics 17(7), Jul. 2012.

Xin, Chen, et al., “Imaging Collector Channel Entrance with a New Intraocular Micro-Probe Swept-Source Optical Coherence Tomography”, Acta Ophthalmologica (2017).

Loewen, Ralitsa T., et al., “Qualification of Focal Outflow Enhancement Using Differential Canalograms”, Quantification of Focal Outflow, vol. 57, No. 6, May 2016.

Kagemann, Larry, et al., “3D Visualization of Aqueous Humor Outflow Structures In-Situ in Humans”, Exp Eye Res; 93(3):308-315. Sep. 2011.

Ishibazawa, Akihiro, et al., “Accuracy and Reliability in Differentiating Retinal Arteries and Veins Using Widefield En Face OCT Angiography”, TVST, vol. 8, No. 3, (2019).

Srienc, Anja I, et al., “Imaging Retinal Blood Flow with Laser Speckle Flowmetry”, Frontiers in Neuroenergetics, vol. 2, Article 128, Sep. 2010.

Kornfield, Tess E., et al., “Regulation of Blood Flow in the Retinal Trilaminar Vascular Network”, The Journal of Neuroscience, Aug. 20, 2014.

Nguyen, Van Phuc et al., “Contrast Agent Enhanced Multimodal Photoacoustic Microscopy and Optical Coherence Tomography for Imaging of Rabbit Choroidal and Retinal Vessels in vivo”, Scientific Reports (2019).

Bouget, David et al., “Vision-Based and marker-Less Surgical Tool Detection and Tracking: A Review of the Literature”, Sep. 13, 2016.

Elmaanaqui, Badr et al., “Birefringence Measurement of the Retinal Nerve Fiber Layer by Swept Source Polarization Sensitive Optical Coherence Tomography”, Optics Express. vol. 19, No. 11, May 23, 2011.

Xu, Benjamin Y. et al., “Deep Neural Network for Scleral Spur Detection in Anterior Segment OCT Images: The Chinese American Eye Study”, TVST, vol. 9, No. 2, Mar. 2020.

Chiang, Bryce et al., “The Suprachoroidal Space as a Route of Administration to the Posterior Segment of the Eye”, Adv Drug Deliv Rev., vol. 126. Feb. 15, 2018.

International Preliminary Report on Patentability for International Application No. PCT/EP2021/075900, dated Mar. 21, 2023, 9 pages.

* cited by examiner

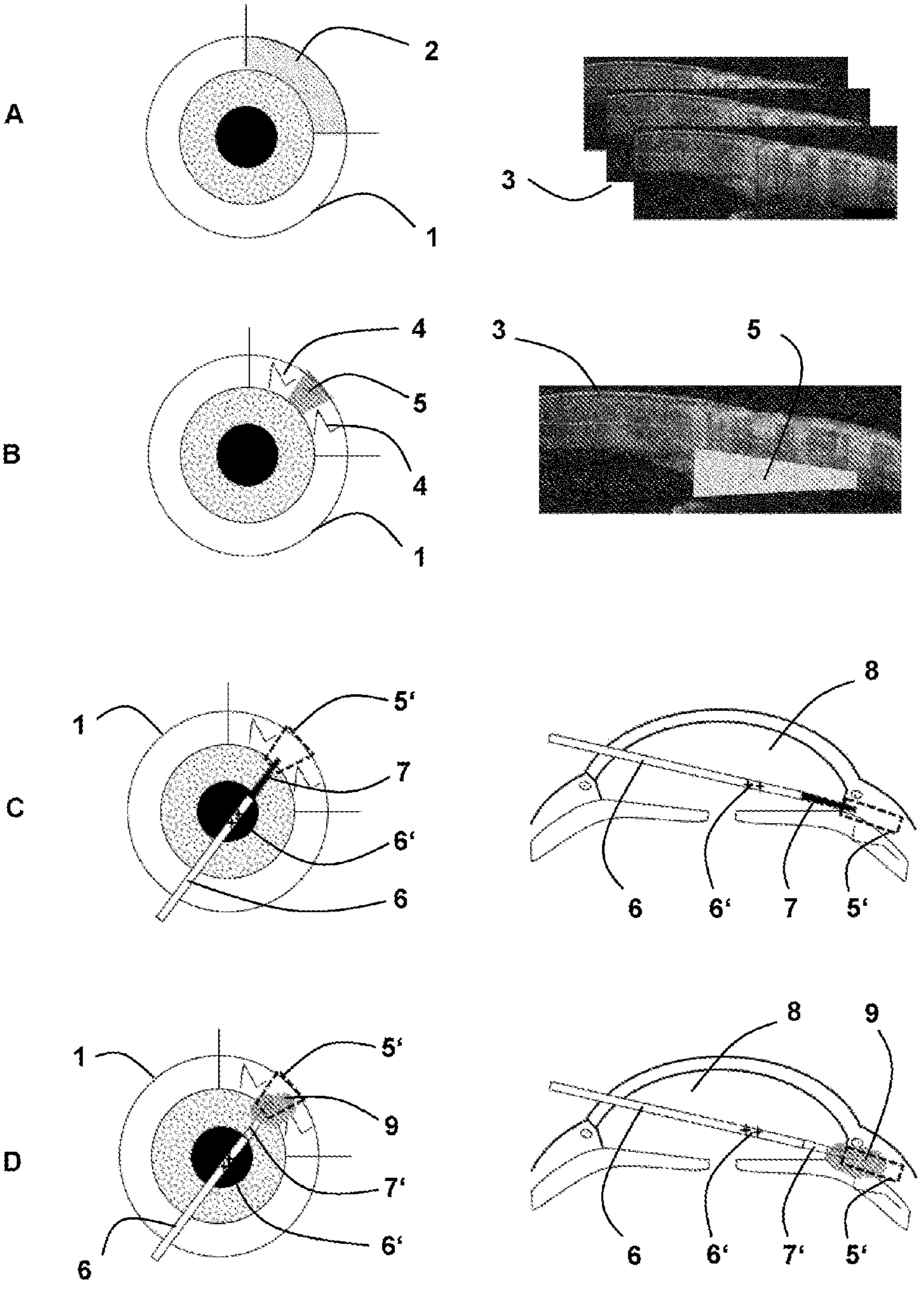
A
2
3
1
B
4
5
3
5
4
1
C
1
5'
7
6'
6
8
6
6'
7
5'
D
1
5'
9
7'
6'
6
8
9
6
6'
7'
5'

DEVICE FOR POSITIONING AN IMPLANT IN A TARGET AREA OF AN EYE

RELATED APPLICATIONS

This application is a National Phase entry of PCT Application No. PCT/EP2021/075900, filed Sep. 21, 2021, which application claims the benefit of priority to U.S. Provisional Application No. 63/080,801, filed Sep. 21, 2020, the entire disclosures of which are incorporated herein by reference

TECHNICAL FIELD

The present invention relates to a device for positioning an implant in a target area of an eye, in particular for glaucoma treatment by aqueous humor drainage from the anterior chamber.

BACKGROUND

Eye implants for drainage of liquid are well known in the prior art. While what are referred to as stents are usually understood as being drainage aids for opening or for keeping open vessels or tissues, what are referred to as shunts serve as drainage aids for bridging, or bypassing, natural drainage paths. However, these functions can also be applied simultaneously or can overlap. According to the invention, the term used below, stent, can thus comprise both functions.

Glaucoma is understood to mean a disease leading to irreversible damage to the optic nerve fibers. In advanced stages, it is even possible for excavation of the optic nerve to occur. Continuously progressive damage to the optic nerve causes a likewise continuous decrease in the field of vision of the patient. Without treatment, this in most cases leads to complete loss of sight.

Although the number of all possible causes of glaucoma or the described damage to the optic nerve is not fully understood at present, one of the most important triggers has been identified as an increase in intraocular pressure caused by deteriorated drainage of aqueous humor within the eye.

As a consequence of such a deteriorated drainage of aqueous humor, that is to say an increased drainage resistance, the pressure within the eye builds up until, with the intraocular pressure now increased, the drainage of aqueous humor is once again in equilibrium with the production of aqueous humor. The relationship between the pressure drop $\Delta P$ that arises over the drainage pathways, given an existing throughflow resistance R and an aqueous humor flow Q, is $\Delta P=R*Q$ here. The changed pressure conditions are then suspected of causing direct damage to the optic nerve through mechanical action, and/or of also causing a reduction in the perfusion pressure, which is important for supplying the optic nerve fibers, in the retina as a result of a changed pressure drop.

A deterioration in the drainage of aqueous humor can be caused, for example, by a narrowing of the iridocorneal angle (narrow-angle glaucoma) or else, in the case of open-angle glaucoma, by changes to the filter tissue of the trabecular meshwork or even the complete blockage thereof (for example in the case of pseudoexfoliation glaucoma or pigmentary glaucoma), or else as a result of a reduction in the cross section of Schlemm's canal or of downstream collector vessels or in the episcleral vascular system. Changes to tissues in the uveoscleral outflow pathway may also lead to a deterioration in the drainage of aqueous humor. Recent investigations also point toward the influence of a third outflow pathway, the uveolymphatic outflow pathway.

A treatment approach under consideration in the treatment of glaucoma is in most cases the reduction of the intraocular pressure. In rarer cases, however, the blood pressure is also adapted.

In the first instance, the intraocular pressure is usually reduced by medication, that is to say using substances which either reduce the production of aqueous humor (for example beta blockers) or else improve drainage through the tissues of the drainage pathways (for example prostaglandins). In recent developments, it is also already the case that prostaglandin analogs (bimatoprost) are embedded in biodegradable polymers and used as implantable medication repository for treating glaucoma (bimatoprost SR with the polymer system poly(D,L-lactide), poly(D,L-lactide-co-glycolide), poly(D,L-lactic acid) and polyethylene glycol 3350).

In the prior art in addition to the numerous other methods for glaucoma treatment, other surgical forms of glaucoma treatment with reduced invasiveness have become known in recent years (micro-invasive glaucoma surgery or else micro-incision glaucoma surgery, or in short: MIGS), these being intended to have a greater potential for pressure reduction in relation to reduced rates of complications, for example through the use of minimally invasive stents and shunts (for example for bridging the trabecular meshwork and for keeping open Schlemm's canal (iStent®, HYDRUS®) or else for drainage from the anterior chamber into the supraciliary space, or suprachoroidal space (CYPASS®, MINIject®, iStent Supra®) or into the subconjunctival space (XEN®, MicroShunt®).

Stents for the suprachoroidal space typically have lengths of 4 to 6.4 mm and implant widths of 0.43 mm (CYPASS®, round) through approximately 1 mm (MINIject®, rectangular with rounded corners) to through approximately 5 mm (STARflo™, planar). The latter, however, is usually no longer considered to be a MIGS device, since it cannot be introduced into the eye with minimal invasion. Thicknesses of suprachoroidal implants are between 0.43 mm (CYPASS®) and 0.6 mm (MINIject®).

Article [1] contains a study on the effectiveness and safety of MINIject® implants in the case of open-angle glaucoma and, in addition to the geometry of the implant, also describes that the implant protrudes approximately 0.5 mm into the anterior chamber after implantation. As is known from other suprachoroidal implants, implants that protrude too far (i.e., 1-2 mm) into the anterior chamber are suspected of contributing to losses of endothelial cells in the cornea, which must be avoided.

The abovementioned surgical interventions are classed here as ab interno and ab externo interventions, depending on whether the manipulation or else the implantation is performed from inside the eye or from outside the eye.

For example, canaloplasty procedures can be performed as ab interno or else ab externo interventions. Examples of drainage aids that can be implanted from inside the eye are iStent®, HYDRUS®, CYPASS® and XEN®, while the MicroShunt® is an example of a drainage aid that can be implanted from outside the eye.

Glaucoma stents or shunts can consist of non-porous materials, for example nitinol, steel, titanium, polyamides, polyethylene glycol and polyurethane (WO 2004/110391 A1), or porous materials, such as biocompatible porous silicones (WO 2017/108498 A1), but can also consist of combinations of these and also contain sensors, for example for the intraocular pressure (U.S. Pat. No. 8,926,510 B2).

An example of a tool for ab interno implantation of a porous implant in the suprachoroidal space is disclosed in WO 2017/108498 A1. In that document, before implantation the implant is compressed in the hollow tool shaft and expands after ejection or positioning in the target tissue. Another example of a tool for ab interno implantation of a tubular implant in the suprachoroidal space is disclosed in EP 3 403 622 B 1.

Reference is also made for example to documents U.S. Pat. No. 6,881,198 B2 and U.S. Pat. No. 3,788,327 A, which describe corresponding surgical implants for lowering the intraocular pressure by drainage of excess aqueous humor.

These surgical implants in the form of stents utilize direct drainage through the cornea, the limbus or the sclera. In this case, the stents may contain a filter membrane in order to ensure a defined outflow.

Devices for treating glaucoma are also described in WO 2016/109639 A2, although the focus there is on additional measures for secure anchoring of such stents in the tissue.

Stents for suprachoroidal use have a greater pressure reduction effect than stents for trabecular use and have the advantage over stents for subconjunctival use that they do not cause damage to the connective tissue and thus keep further treatment options open. Stents for suprachoroidal use also require no wound modulation through the use of substances that control scarring, such as mitomycin C.

A disadvantage of stents for suprachoroidal use is that the progressions in pressure reduction that can be achieved are extremely difficult to predict. The problems in particular are possible transient strong pressure drops (hypotonia) or pressure increases (hypertonia). In halting hypotonia (<5 mmHg), serious complications through to retinal detachments can occur. Hypertonia, on the other hand, leads to progression of the glaucoma.

The cause of the problems is usually the production, but also possible sudden closure, of a cyclodialysis cleft, torn open by the implantation, between detached ciliary muscle fibers and the scleral spur, which can result in a strong outflow of aqueous humor from the anterior chamber directly into the suprachoroidal space.

A further disadvantage of stents for suprachoroidal use, which should not be underestimated, is that the implantation of such stents may occasionally lead to injury to important eye structures (vessels, muscles, nerves), in particular to the root of the iris and vessels that lead from the choroid to the sclera. Additionally, some tissue regions may be disadvantageous for implantations as a result of earlier interventions by scarring processes as the tissue may raise significant resistance to an implantation, and this should be avoided.

The present invention is based on the object of developing a solution for positioning an implant in a target area, through which it is possible, for example, to significantly reduce or even exclude the risk of injury to important structures, such as vessels, muscles, and nerves. In addition to bleeding (hemorrhage, hyphema) as a consequence of vessel injuries during the implant of stents, for example in the suprachoroidal space, injuries to the root of the iris, for example, are also critical since these may entail damage to the pupil function and hence significant impairments of the faculty of sight.

A further object is the avoidance of damage during the implantation of other types of implants, for example medicament stores, for treating the glaucoma (Glaukos iDose®) or else the age-related macular degeneration (Genentech/Roche port delivery system).

Similar problems as a result of tissue damage (such as vessel injury) as a consequence of malpositioning may also occur during catheterization, for example during canaloplasties for glaucoma treatment, or else in the case of subretinal catheterization, for example for the purpose of stem cell or gene therapy of retinal diseases, for example AMD or retinitis pigmentosa or for the purposes of medication [13].

SUMMARY

Example embodiments of the present invention for positioning an implant in a target area of an eye include an image recording unit, an image display unit, a control and evaluation unit, and an implantation tool for receiving and inserting the stent implant. The image recording unit is designed to make available at least intraoperative recordings of the target area. The control and evaluation unit is designed to detect important eye structures in these intraoperative recordings or available preoperative recordings of the target area and to propose or select a target region for the implant. The control and evaluation unit is further designed to generate navigation data for the insertion of the implant contained in the implantation tool into the proposed or selected area from the intraoperative recordings. The image display unit is designed to display the intraoperative recordings of the target region made available by the image recording unit and the navigation data made available by the control and evaluation unit.

A first group of example embodiments relates to the image recording unit, which is designed to make available two-dimensional recordings, but also three-dimensional recordings.

Furthermore, the image recording unit is designed to make available both preoperative and intraoperative recordings which are based on optical coherence tomography (hereinafter OCT) or ultrasonic volume scans and/or based on two-dimensional imaging methods (camera, color camera, stereo camera, confocal scanners, or line scanners, for example), and also with the use of fluorescent dyes.

In the process, the imaging method should have a sufficiently large penetration depth into the tissue in order to be able to capture the target area as completely as possible, even if a partial capture of the target area would already offer a reduction in the risk of injury to important eye structures.

Therefore, light-based imaging methods may use those wavelengths which are absorbed as little as possible in aqueous humor and in the tissue. Wavelengths such as those between 1000 and 1100 nm, with which penetration depths of up to a few millimeters can be realized, are suitable for this purpose for eye tissues such as the choroid. Methods such as ultrasound can penetrate deeper into the tissues (millimeters to centimeters) but have in turn a lower spatial resolution.

Therefore, the image recording unit can also be designed so that it combines different imaging methods, for example an OCT at 1060 nm with ultrasonic imaging using an 18 MHz transducer.

The realization of a penetration depth of the imaging that reaches the length of the implant can be used by virtue of being able to realize imaging which can be implemented largely along the insertion direction and can then be used very intuitively, in a manner similar to "night vision equipment for important eye structures".

Should this not be possible or desirable, lateral imaging is also possible, for example in transscleral fashion. However, these recordings obtained in transscleral fashion can in turn be converted by the control and evaluation unit into representations (for example, by transformations such as rotations, distortion, and size adjustment, or by overlaying and masking of identified or segmented eye structures), which can then in turn be superimposed on the normal representations of the surgical microscope for example.

Ultrasonic methods and light-based imaging methods using wavelengths longer than 1060 nm (for example an OCT at 1310 nm or even 1550 nm), are suitable for transscleral imaging since this allows the scattering in the tissue to be further reduced while the absorption in the aqueous humor plays a lesser role as a result of the shortened path to the target area.

A second group of example embodiments relates to the control and evaluation unit, which is designed to detect and/or classify vessels in the recordings transmitted by the image recording unit, and/or to determine the distances between said vessels and/or to distinguish between arteries and veins in order to select a target region for the introduction of the stent implant. Further, the control and evaluation unit is designed to mark the selected target region with a target marking in the representation by way of the image display unit. By way of example, this target marking can be a representation of a frame of contrasting color, as a superposition in the representation of the tissues in the target region (for example, the suprachoroidal space). In certain embodiments, the control and evaluation unit is additionally designed to select the implant in respect of shape, dimension, type, material, manageability, etc. on the basis of the selected target region.

A third group of example embodiments relates to the image display unit which is designed to display both the preoperative and intraoperative recordings on a monitor and/or in eyepieces of a microscope.

A last group of example embodiments relates to the implantation tool which additionally comprises an endoscope for introducing the implant into the target region more safely. By way of example, this may contain imaging for recognizing important eye structures, such as vessels, in the vicinity of the implantation tool (e.g., color camera, OCT or ultrasound able to image eye structures located 0.2 millimeters to 2 cm in front of the tip of the implantation tool or implant) in order to avoid an injury to these structures. Furthermore, the tip or the shaft or other parts of the implantation tool may comprise markers to facilitate the introduction of the implant into the target region. In certain example embodiments, the implant may also comprise such a marker.

Methods that use image recording units, both using markers and not using markers, are known for tracking surgical tools in relation to anatomical structures [10]. Moreover, landmarks such as iris structures, vessel structures (branchings or crossings) in the conjunctiva, choroid or retina, or else light reflections on the cornea, which are able to be tracked by stereo camera or OCT, for example, are suitable for tracking human eyes.

In accordance with certain example embodiments, the device for positioning a stent implant for glaucoma treatment by way of aqueous humor drainage into the suprachoroidal space is a surgical microscope.

The proposed device for positioning an implant may be provided for the implantation of stent implants into the suprachoroidal space but can also be used for the positioning of shunt or stent implants in other areas of the eye, in order to be able to significantly reduce or even exclude the risk of bleeding (hemorrhage, hyphema) as a consequence of vessel injury or else injury to constituent parts of the eye.

BRIEF DESCRIPTION OF THE DRAWINGS

The invention is described in more detail below on the basis of example embodiments and with reference to the accompanying drawings, which also disclose features of the invention. In this respect, FIGS. 1A, 1B, 1C, and 1D depict the schematic course of events when planning and carrying out the positioning of a stent implant into the suprachoroidal space.

DETAILED DESCRIPTION

The proposed device for positioning an implant in a target area of an eye comprises an image recording unit, an image display unit, a control and evaluation unit, and an implantation tool for receiving and positioning the implant to be introduced.

According to the invention, provided as the target areas are not only the anterior chamber but also the suprachoroidal space, the subconjunctival space, the trabecular meshwork, Schlemm's canal, and the cornea and the limbus.

The image recording unit is designed to make available preoperative and/or intraoperative recordings of the target area.

First of all, the control and evaluation unit is designed to detect important eye structures in the preoperative recordings of the target area provided by the image recording unit and to propose or select a target region for the implant.

Further, the control and evaluation unit is designed to use the intraoperative recordings made available by the image recording unit to generate navigation data for the introduction of the implant contained in the implantation tool into the proposed or selected target region.

The image display unit is designed to display the intraoperative recordings of the target area of an eye made available by the image recording unit and the navigation data made available by the control and evaluation unit.

In accordance with a first example embodiment, the image recording unit is designed to make available at least intraoperative recordings which are based on OCT or ultrasonic volume scans and/or on two-dimensional imaging methods, and also using fluorescent dyes. However, it is possible that the image recording unit also makes preoperative recordings available.

The recordings made available should in this case be two-dimensional, but may be three-dimensional in other embodiments, and fully contain the target area of the eye. This also includes two-dimensional or three-dimensional film sequences.

In this case, the image recording unit should also comprise the illumination required for the image recording; this is assumed below. Illuminations, which are not perceivable or hardly perceivable by the patient, may have a low phototoxicity or a trivial thermally damaging effect but should also have a sufficient transmission through the cornea and transparent eye media. The use of light with the wavelengths of 350 to 1550 nm is possible, for example the use of 800 to 1100 nm. Examples of usable light sources are halogen lamps, incandescent lamps, LEDs with suitable filtering, but also superluminescent diodes (hereinafter SLDs) or lasers.

In this case, the OCT scans may contain the usual structure information (i.e., the representation of the scattering intensities or amplitudes) but also flow information obtained by way of the evaluation of phase and speckle variations (OCT angiography, hereinafter OCTA) or else deformation or elasticity information in different tissue regions (for example optical coherence elastography, hereinafter OCE). In addition to the OCT system, OCE requires mechanical excitation options, for example a sample deformation by eye movement or else mechanical excitation (e.g., plunger), or else ultrasonic excitation. Flow information can also be obtained from ultrasonic Doppler recordings, albeit with a lower spatial resolution than in the case of OCTA.

As described in [9], the application of photoacoustic imaging, including the use of contrast-enhancing agents such as certain gold nanoparticles, is also possible to this end.

Although this requires much outlay, it is also possible to use 3-D magnetic resonance imaging (hereinafter MRI), optionally also with the application of contrast agents such as gadolinium.

The control and evaluation unit is designed to detect important eye structures, such as vessels, muscles, nerves, or portions of the root of the iris, of the trabecular meshwork, of Schlemm's canal, or of the scleral spur, in the preoperative recordings made available by the image recording unit. By way of example, such structures can be detected on the basis of typical speckle structures in OCT recording, which speckle structures arise as a result of characteristic single and multiple scattering at the tissue structures, or else on the basis of characteristic birefringence, for example at nerve fibers [11].

The identification of anatomical structures such as the scleral spur in OCT recordings can also be implemented here by neural networks [12].

However, vessels are detected and/or classified and/or the distances between the vessels are determined and/or arteries and veins are distinguished, for example, in order to select a target region for the introduction of the implant.

In this case, a sufficiently short time (less than 0.2 seconds, such as, but not limited to, less than 0.1 seconds or less than 0.04 seconds) may elapse from the recording of the intraoperative recording via the processing in the control and evaluation unit to the display of the derived navigation data in order to allow a sufficiently fast reaction to changes in the position that arise during the operation and in order to allow a fluid representation of navigation data. By way of example, such changes in position may arise as a result of unwanted eye movements, which cannot be completely precluded even under anesthesia, or else as a result of a collapse of the eye in the eye socket as a consequence of an intermittently insufficiently compensated aqueous humor outflow through the microincision.

In addition to the proposition or the selection, by the device according to the invention, of the advantageous target region for the implantation, it is also possible to allow a manual selection of the target region by the surgeon, and only provide a warning in the case of an imminent injury to important eye structures, for example the root of the iris, or optionally not allow the selection of the target area, for example by virtue of a release of the implantation tool not being allowed. Further, there may also be a warning if there is an unwanted deflection of the implant from the sought-after path to the target region during the positioning, for example as a result of the implant coming across hardened tissues (for example as a consequence of earlier scarring) or else as a result of an unexpected perforation of tissue layers (e.g., Schlemm's canal). Furthermore, there may be a warning regarding, or a non-admittance of, a potential target region if known risk situations are present, for example the presence of a cyclodialysis cleft or a comparatively thin choroid in the case of a myopic patient, which increases the risk during implantations in the suprachoroidal space.

There is also the option of the control and evaluation unit receiving preoperative data from another image recording system (e.g., a tabletop OCT apparatus) and the selection of the target region being implemented on the basis of these data. It is likewise possible for the target region to be implemented on the basis of preoperative recordings on another system (e.g., on the tabletop apparatus) and only for coordinates of the target region to be transferred to the device according to the invention.

The preoperative determination of the position of vessels allows the selection of potential areas in which fewer or smaller vessels are located with greater spacings, thus allowing the risk of vessel injury to be minimized or excluded.

The vessels, for example, are distinguished in this case according to size classes and vessel type (i.e., arteries or veins). The different spectral properties on account of different oxygen saturation levels in the blood, for example, are suitable to make this distinction, or else the different flow behavior that is measurable by OCT angiography [8] or speckle flowmetry [7], for example, for example the different flow speeds and different pulsations of vessel diameters or else small movements of the surrounding tissue, depending on the heartbeat. According to [8], structural information is also suitable for distinguishing between vessel types, for example:

- the presence of hypointense regions in the representation of OCT angiography, which represent capillary vessel-free zones, which are associated with arteries,
- the fact that arteries do not cross other arteries, and
- the tracing-back to larger vessels of an already identified type.

It is also possible, as is known from retinal angiography, to locally or systemically inject dyes such as fluorescein or else indocyanine green, for example, and to use the temporally different onset of fluorescence in the case of suitable light excitation for the purposes of distinguishing between arteries and veins.

An example respective size threshold may be defined for the various vessel types, above which there should, where possible, no longer be any vessel injury as a result of the implantation. By way of example, injury to small capillaries may be acceptable, whereas the injury to large vessels, such as arteries at the root of the iris, should be precluded. In this case, the size class can be realized from diameter measurements on the vessels, for example from chamber angle or OCT recordings, or else by way of the classification of the vessel order according to the number of vessel branching of relatively large vessels, for example the central eye vessels, down to the vessel to be classified [8]. Indirectly, the flow speed linked to the vessel diameter can also be used for size classification purposes, for example to avoid the injury to vessels with a fast blood flow.

OCT volume scans or else recordings using fluorescent dyes (fluorescein, NAF, ICG) may be used for the preoperative recordings made available by the image recording unit. Once again, this includes film sequences.

Furthermore, trials are known with regards to determining the position of collector vessels by phase-sensitive [2] or endoscopic [3] OCTs, with the aid of which stents (e.g., iStent®) should then be effectively positioned in the trabecular meshwork, especially in the case of a collapsed Schlemm's canal. However, it is not important here to avoid vessel injuries but to have the stent to be implanted as close as possible to one of the collection vessels in order to promote the aqueous humor drainage. Here, these collection vessels are not situated in the target area provided for this implantation (trabecular meshwork) and consequently do not represent a risk to be avoided as a consequence of vessel injury during the implantation either.

It is furthermore known in this context that, according to [4], both the trabecular outflows and the vascular vessel system relevant to the (trabecular) drainage of the aqueous humor [5] can be represented in vitro.

In accordance with a second example embodiment, the control and evaluation unit is designed to propose or even select an alternative target region for the introduction of the implant. Such an alternative target region can have a statistically lower risk for complications and/or injure fewer important eye structures than a first target region, which has been chosen by the surgeon themselves for example.

However, the control and evaluation unit may also further be designed to select the implant in respect of shape, dimension, type, material, manageability, etc. on the basis of the selected target region. In this case, it is not only flexible stent implants that should be considered, but also compressible variants such as XEN® and MINIject®.

The selection of an implant type in respect of dimensions, flow resistance or the like is implemented on the basis of the properties of the target region. For example, an implant with a greater flow resistance (for example realized by way of a smaller flow cross-section) is thus required in the case of the thin choroid since this tissue is "more absorbent" in this case.

In one example, the control and evaluation unit may be further designed to mark the proposed or selected target region with a target marking in the representation by way of the image display unit. In another example, the tip of the implantation tool and/or the implant may comprise markers that can be detected by the image recording unit in order to facilitate the introduction of the implant into the target region represented by the target marking. To this end, the marker needs to be able to be recorded by way of the image recording unit (suitable spectral characteristic or color), needs to be able to be identified by the control and evaluation unit, and needs to be able to be represented by way of the image display unit, in one example together with the target marking representing the target region.

As already described, the control and evaluation unit is also designed to use the intraoperative recordings made available by the image recording unit to generate navigation data for the introduction of the implant contained in the implantation tool proposed or selected target region of the.

In this case, the navigation of the implantation tool to the selected (and marked) target region is implemented intraoperatively for the surgeon by direction and/or relative position specifications, or else by way of appropriate control pulses for an implantation robot, in which the implantation tool is moved by a movement unit in accordance with the navigation data in the form of control signals.

To this end, tracking of the eye and of the implant and/or of the implantation tool in relation to one another is required.

In one example, the implantation tool may be designed so that the implant can be introduced into the eye through a microincision (similar to MICS cataract surgery, that is to say through an incision of less than 1.8 mm or else 1.4 mm width) in order to realize an ab interno implantation, for example into the suprachoroidal target tissue, on the opposite side of the anterior chamber.

Moreover, the introduction of the implant into the target area can be simplified if the tip of the implantation tool additionally comprises an endoscope.

Since it is necessary to pay attention to the correct depth, especially when implanting a stent implant into the suprachoroidal space, tolerances to be observed accordingly should be observed in this respect. For each stent implant, these should be saved in the control and evaluation unit or else be determined by the control and evaluation unit from the encountered position of important eye structures, for example vessels. In the case of implants with lengths of the order of 5 mm, accuracies of 10 μm to 500 μm, for example, approximately 250 μm, are required in relation to the depth positioning. Required positioning accuracies in other spatial directions, for example along the trabecular meshwork, can be substantially larger and also be of the order of millimeters.

In accordance with a further example embodiment, the image display unit is designed to display both the preoperative and intraoperative recordings and the navigation data on a monitor and/or in eyepieces of a microscope and/or a head-mounted display (a visual output apparatus to be worn on the head; hereinafter HMD).

In accordance with another example embodiment, the device for positioning a stent implant for glaucoma treatment by way of aqueous humor drainage into the suprachoroidal space is a surgical microscope (hereinafter OPMI), which comprises an image recording unit, an image display unit, a control and evaluation unit, and an implantation tool for receiving the stent implant to be introduced.

According to the invention, the image recording unit thereof is designed to intraoperatively make available both recordings of eye structures based on two-dimensional imaging and OCT-based volume scans of eye structures. Such eye structures relevant to the implantation of stent implants are:

- for trabecular meshwork stents: the chamber angle of the eye with trabecular meshwork, Schlemm's canal and structures therebehind, such as the aqueous humor collection vessels and the subsequent episcleral venous system.
- for suprachoroidal stents: scleral spur, root of the iris, Schwalbe's line, arterial ring around the iris, the vessels supplying the ciliary body (e.g., the anterior ciliary vein), optionally also the ciliary muscles, the ciliary process, zonular fibers, and the natural or artificial lens, and the capsular bag,
- for implants possibly protruding into the anterior chamber, such as suprachoroidal stents or tube shunts: corneal layers and surfaces, such as the posterior corneal surface or the endothelial cell layer, and
- for subconjunctival stents: choroid and conjunctiva with vessels
- for the limbus or the cornea: blood and lymph vessels, for example as a consequence of neovascularizations following inflammations, or else locally reduced density of corneal endothelial cells.

The control and evaluation unit is designed to detect vessels in a preoperative volume scan of the suprachoroidal space of the eye and to select a target region for the stent implant and to generate navigation data for the insertion of the stent implant contained in the implantation tool into the selected target region in the suprachoroidal space from the intraoperative recordings and volume scans.

The image display unit is designed to display the intraoperative recordings and/or volume scans of the suprachoroidal space made available by the image recording unit and the navigation data made available by the control and evaluation unit on a monitor and in the surgical microscope eyepieces.

According to the invention, there is an intraoperative determination of the vessel positions on the basis of a preoperative OCT/OCTA volume scan. Optionally, the visualization can be further improved by the use of additional dyes (NAF, ICG or the like) and/or by the use of an endoscope.

According to the invention, an implantation into the suprachoroidal space is guided by a surgical microscope-assisted navigation on the basis of planning data obtained preoperatively, in such a way that there cannot be any injury, or only minor injuries, to vessels.

Furthermore, should bleeding nevertheless occur, the images of the surgical microscope can be adapted to the effect of the stent implant still being displayed in relation to the target region despite the impaired view for the surgeon, for example by way of displaying a stent marking representing the stent implant in relation to the target marking representing the target region. This target marking, in turn, can likewise still be displayed despite the bleeding by virtue of being displayed in relation to natural or artificial markers or landmarks in the eye, which are still visible despite the bleeding or the position of which can still be determined. Additionally, movement notifications for completing the intervention may be provided.

In this respect, FIGS. 1A, 1B, 1C, and 1D show the schematic course of events when planning and carrying out the positioning of a stent implant into the suprachoroidal space.

Symbolically, FIG. 1A shows a frontal view of an eye 1 which has the sector 2 marked, from which sector the adjacently displayed (real) preoperative OCT scans 3 (radial sections through the anterior chamber angle from an OCT volume scan) originate. These OCT scans 3 contain regions in which vessels are located and also vessel-induced artifacts ("shadows in the OCT signal under the vessels"). In reality, these regions are highlighted accordingly by color.

FIG. 1B shows a frontal view of the eye 1, in which not only detected vessels 4 but also the selected target region 5 are depicted. Depicted adjacently there is a (real) preoperative or intraoperative obtained OCT scan 3 (radial section through the anterior chamber angle from an OCT volume scan), likewise with the selected target region 5 in a side view.

FIG. 1C in turn shows the eye 1 according to FIG. 1B. However, the target marking 5' (dashed line) for the target region is depicted here. The stent implant 7 and the implantation tool 6 with a marker 6' are also depicted. Next to it, FIG. 1C symbolically depicts the anterior chamber 8 of the eye 1 in a sectional representation. The target marking 5' of the target region, the stent implant 7 and the implantation tool 6 with the marker 6' are also depicted here.

In this case, the target region 5 is dimensioned so that it receives the desired stent implant 7, or else the dimension of the stent implant 7 is matched to the available, vessel-free target region 5.

FIG. 1D shows the eye 1 and its anterior chamber 8 according to FIG. 1C. In addition to the target marking 5' for the target region, the stent implant 7 now comprises a stent marking 7' (dashed line). Additionally, FIG. 1D shows an arisen instance of bleeding 9, which makes a direct representation of the target region 5 more difficult or prevents the latter. Despite the arisen instance of bleeding 9, the stent implant 7 can be navigated into and implanted in the target region marked by the target marking 5', by way of the stent marking 7' depicted in relation to markers 6' and the recommendations for movement directions. Analogously, the sectional representation of the anterior chamber 8 shows the implantation tool 6 and the stent marking 7' depicted in relation to the marker 6' and the target marking 5' despite the bleeding 9.

The symbolic frontal and sectional representations can be replaced in the device according to the invention with real intraoperative recordings, which can be depicted by the image display unit, for example overlaid with semitransparent, colored target markings 5' and stent markings 7' (as areas or frames).

The device according to the invention makes available a solution for the glaucoma treatment by way of aqueous humor drainage from the anterior chamber into the suprachoroidal space, which device enables safe positioning of a stent implant.

By way of the present device, it is possible to significantly reduce or even exclude the risk of bleeding (hemorrhage, hyphema) as a consequence of vessel injury during the implantation of stents into the suprachoroidal space. Should there nevertheless be unexpectedly strong bleeding, the implantation can be safely and correctly completed despite the blood obscuring the view.

The most advantageous target area for the stent implant is selected on the basis of preoperative planning and said stent implant is implanted in this target area by way of intraoperative navigation.

Even though the proposed device for positioning a stent implant into the suprachoroidal space, said device can also be used for the positioning of shunt or stent implants in other areas of the eye, in order to be able to significantly reduce or even exclude the risk of bleeding (hemorrhage, hyphema) as a consequence of vessel injury or else injury to constituent parts of the eye.

LITERATURE

[1] Denis et al; "A First-in-Human Study of the Efficacy and Safety of MINIject in Patients with Medically Uncontrolled Open-Angle Glaucoma (STAR-I)"; Ophthalmology Glaucoma Volume 2, Number 5, September/October 2019; 290-297; doi.org/10.1016/j.ogla.2019.06.001

[2] Li et al; "Phase-sensitive optical coherence tomography characterization . . . "; Journal of Biomedical Optics 17(7), 076026 (July 2012); doi.org/10.1117/1.JBO.17.7.076026

[3] Xin et al; "Imaging collector channel entrance with a new intraocular micro-probe swept-source optical coherence tomography"; Acta Ophthalmologica 2017; 603-607; DOI: 10.1111/aos.13415

[4] Loewen et al; "Quantification of Focal Outflow Enhancement Using Differential Canalograms"; IOVS j May 2016 j Vol. 57 j No. 6 j 2831 doi: 10.1167/iovs.16-19541

[5] Kagemann et al; "3D Visualization of Aqueous Humor Outflow Structures In-Situ in Humans"; Exp Eye Res. 2011 September; 93(3): 308-315. doi:10.1016/j.exer.2011.03.019

[6] Ishibazawa et al. "Accuracy and Reliability in Differentiating Retinal Arteries and Veins Using Widefield En Face OCT Angiography", doi:https://doi.org/10.1167/tvst.8.3.60

[7] Srienc et al., "Imaging retinal blood flow with laser speckle flowmetry", https://doi.org/10.3389/fnene.2010.00128

[8] Kornfield and Newman, "Regulation of Blood Flow in the Retinal Trilaminar Vascular Network", doi: 10.1523/JNEUROSCI.1971-14.2014

[9] Nguyen et al., "Contrast Agent Enhanced Multimodal Photoacoustic Microscopy and Optical Coherence Tomography for Imaging of Rabbit Choroidal and Retinal Vessels in vivo", doi: 10.1038/s41598-019-42324-5

[10] Bouget et al., "Vision-based and marker-less surgical tool detection and tracking: a review of the literature", DOI: 10.1016/j.media.2016.09.003

[11] Elmaanaoui et al., "Birefringence measurement of the retinal nerve fiber layer by swept source polarization sensitive optical coherence tomography", doi: 10.1364/OE.19.010252

[12] Xu et al., "Deep Neural Network for Scleral Spur Detection in Anterior Segment OCT Images: The Chinese American Eye Study", doi:https://doi.org/10.1167/tvst.9.2.18

[13] Chiang et al., "The suprachoroidal space as a route of administration to the posterior segment of the eye", doi: 10.1016/j.addr.2018.03.001

The invention claimed is:

1. A device for positioning a stent implant in a target area of an eye, comprising:

an image recorder;

an image display;

a controller and evaluator; and an implantation tool that receives the stent implant and inserts the stent implant into the target area;

wherein the image recorder is configured to generate recordings of the target area;

wherein the controller and evaluator is configured to detect eye structures in the recordings of the target area and to propose or select a target region for the stent implant;

wherein the controller and evaluator is further configured to generate navigation data from the recordings to insert the stent implant contained in the implantation tool into the target region, and wherein the image display is configured to display the recordings and the navigation data.

2. The device as claimed in claim 1, wherein the target area is selected from the group consisting of: a suprachoroidal space, a subconjunctival space, a trabecular meshwork, Schlemm's canal, a limbus, and a sclera.

3. The device as claimed in claim 1, wherein the eye structures are selected from the group consisting of: vessels, muscles, nerves, and portions of a root of the iris, of a trabecular meshwork, of Schlemm's canal, or of a scleral spur.

4. The device as claimed in claim 1, wherein the recordings are selected from the group consisting of: preoperative recordings, intraoperative recordings, and any combination thereof.

5. The device as claimed in claim 4, wherein the recordings are made based on a method selected from the group consisting of: OCT, ultrasonic volume scans, two- dimensional imaging, three-dimensional imaging, imaging using fluorescent dyes, and any combination thereof.

6. The device as claimed in claim 1, wherein the image recorder is configured to generate two-or three-dimensional recordings.

7. The device as claimed in claim 1, wherein the controller and evaluator is configured to propose or select the target region by a method selected from the group consisting of: detecting blood vessels, classifying blood vessels, determining spacings of blood vessels, determining concentration of blood vessels, distinguishing between arteries and veins, and any combination thereof.

8. The device as claimed in claim 1, wherein the controller and evaluator is further configured to propose or select an alternative target region for introduction of the stent implant.

9. The device as claimed in claim 1, wherein the controller and evaluator is further configured to select an aspect of the stent implant based on the target region, wherein the aspect is selected from the group consisting of: shape, dimension, type, material, manageability, and any combination thereof.

10. The device as claimed in claim 1, wherein the image display is configured to display the recordings on a display selected from the group consisting of: a monitor, eyepieces of a microscope, a head-mounted display, and any combination thereof.

11. The device as claimed in claim 1, wherein the controller and evaluator is further configured to mark the target region with a target marking.

12. The device as claimed in claim 1, wherein at least one of the implantation tool and the stent implant comprises at least one marker detectable by the image recorder.

13. The device as claimed in claim 1, wherein the controller and evaluator is further configured to facilitate achieving necessary positioning accuracy within a scope of positioning of the stent implant by generating intraoperative navigation data on the basis of at least one of the group consisting of: a target marking the target region, at least one marker detectable by the image recorder, and any combination thereof.

14. The device as claimed in claim 1, wherein a positioning accuracy to be achieved when inserting the stent implant is stored in the controller and evaluator for each stent implant.

15. The device as claimed in claim 1, wherein a tip of the implantation tool additionally comprises an endoscope to facilitate introducing the stent implant into the target region.

16. The device as claimed in claim 1, wherein less than 0.2 seconds elapse between a start of an intraoperative recording by the image recorder and a display on the image display of the navigation data derived from the intraoperative recording.

17. A surgical microscope for positioning a stent implant in a target area of an eye, comprising:

an image recorder;

an image display;

a controller and evaluator; and an implantation tool that receives the stent implant to be inserted;

wherein the image recorder is configured to generate an imaging of the target area, wherein the imaging comprises two-dimensional intraoperative imaging recordings or OCT-based volume scans of the target area, wherein the controller and evaluator is configured to detect eye structures in an intraoperative volume scan of the target area and to propose or select a target region for the stent implant;

wherein the controller and evaluator is further configured to generate navigation data for insertion of the stent implant into the target region from the imaging; and wherein the image display is configured to display the imaging and the navigation data on at least one of a monitor, eyepieces of a microscope, a head-mounted display, or any combination thereof.

18. A device for positioning a stent implant in a target area of an eye, comprising:

an image recorder;

a controller and evaluator;

an implantation tool that receives the stent implant and inserts the stent implant; and a movement unit for the implantation tool, wherein the image recorder is configured to generate recordings of the target area;

wherein the controller and evaluator is configured to detect eye structures in the recordings of the target area and to propose or select a target region for the stent implant;

wherein the controller and evaluator is further configured to generate navigation data from the recordings to insert the stent implant contained in the implantation tool into the target region, and wherein the controller and evaluator is configured to convert the navigation data into control signals for the movement unit.

* * * * *